US006033661A

United States Patent [19]
Smith et al.

[11] Patent Number: 6,033,661
[45] Date of Patent: Mar. 7, 2000

[54] COMPOSITION AND METHOD FOR ALLOGENETIC MONONUCLEAR CELL IMMUNOTHERAPY

[75] Inventors: J. Bruce Smith, Philadelphia, Pa.; John G. Fort, Glenview, Ill.

[73] Assignee: Thomas Jefferson University, Philadelphia, Pa.

[21] Appl. No.: 08/881,268

[22] Filed: Jun. 24, 1997

Related U.S. Application Data

[62] Division of application No. 08/476,698, Jun. 7, 1995, Pat. No. 5,674,487.

[51] Int. Cl.$^7$ ............................. C12N 5/08; C12N 5/06
[52] U.S. Cl. ................ 424/93.71; 424/93.7; 435/372; 435/372.2; 435/372.3
[58] Field of Search ........................ 424/93.7, 93.71; 435/372, 372.2, 372.3

[56] References Cited

U.S. PATENT DOCUMENTS

| 4,996,194 | 2/1991 | Cohen et al. ........................ 514/21 |
| 5,004,681 | 4/1991 | Boyse et al. ........................ 435/2 |
| 5,114,721 | 5/1992 | Cohen et al. ........................ 424/534 |

OTHER PUBLICATIONS

Nuovo et al., PCR Methods Appl. 2(4): 305–312 (1993).
Boldt, Mol. Immunol. 17(1): 47–55 (1980).
Syren et al., Acta Haematol. 4(1): 29–35 (1971).
Vainchenker et al., Blood Cells 5: 25–42 (1979).
Abramsky, O., "Pregnancy and Multiple Sclerosis", *Ann. Neurol.* 1994, 36, S38–S41.
Bernardi et al., "The influence of pregnancy on relapses in multiple sclerosis: a ccohort study", *Acta Neurol. Scand.* 1991, 84, 403–406.
Birk et al., "The Clinical Course of Multiple Sclerosis During Pregnancy and the Puerperium", *Arch. Neurol.* 1990, 47, 738–742.
Connelly, J.F., "Interferon Beta for Multiple Sclerosis", *Ann. Pharmacother.* 1994, 28, 610–616.
Davis and Maslow, "Multiple Sclerosis in Pregnancy: A Review", *Obstet. Gynecol. Surv.* 1992, 47, 290–296.
Durelli et al., "Chronic systematic high–dose recombinant interferon alfa–2a reduces exacerbation rate, MRI signs of disease activity, and lymphocyte interferon gamma production in relapsing–remitting multiple sclerosis", *Neurology* 1994, 44, 406–413.
Elliott et al., "Treatment of Rheumatoid Arthritis with Chimeric Monoclonal Antibodies to Tumore Necrosis Factor α", *Arthritis Rheum.* 1993, 36, 1681–1690.
Goldberg et al., "Alloantibody Responses to Antigens Recognized by Rabbit Antitrophoblast Antisera in Trophoblast and Mononuclear Cell (MNC) Membranes by Primary Aborting Women Before and After Paternal Leukocyte Immunization", *Am. J. Reprod. Immunol.* 1995 33:21–30.
Goldberg et al., "Immunological Effects of High Dose Administration of Anti–CD4 Antibody in Rheumatoid Arthritis Patients", *J. Autoimmunity* 1991, 4, 617–630.

Hench in *Mayo Clin. Proc.*, "The Ameliorating Efect of Pregnancy on Chronic Atrophic (Infectious Rheumatoid) Arthritis, Fibrosis, and Intermittent Hydrarthrosis", 1938, 13, 161–167.
Horneff et al., "Treatment of Rheumatoid Arthritis with An Anti–CD4 Monoclonal Antibody", *Arthritis Rheum.* 1991, 34, 129–140.
Herzog et al., "Anti–CD4 Antibody Treatment of Patients with Rheumatoid Arthritis: I. Effect on Clinical Course and Circulating T Cells", *J. Autoimmunity* 1989, 2, 627–642.
Hutchinson, M., "Pregnancy in multiple sclerosis", *J. Neurol Neurosurg. Psychiatry*, 1993, 56, 1043–1045.
Jameson et al., "A rationally designed CD4 analogue inhibits experimental allergic encephalomyelitis", *Nature* 1994, 368, 744–746.
Karsh et al., "Lymphapheresis in Rheumatoid Arthritis", *Arthritis Rheum.* 1981, 24, 867–873.
Kingsley and Verwilghen, "T cell vaccination in humans", *Clin. Exp. Rheumatol.* 1993, 11, S63–S64.
Lohse et al., "Induction of an Anti–Vaccine Response by T Cell Vaccination in Non–human Primates and Humans", *J. Autoimmunity* 1993, 1, 121–130.
Moreland et al., "Use of a Chimeric Monoclonal Anti–CD4 Antibody in Patients with Refractory Rheumatoid Arthritis", *Arthristis Rheum.* 1993, 36, 307–318.
Nelson et al., "Maternal–Fetal Disparity in HLA Class II Alloantigens and the Pregnancy–induced Amelioration of Rheumatoid Arthritis", *N. Eng. J. Med.* 1993, 329, 466–471.
Nepom et al., "HLA Genes Associated with Rheumatoid Arthritis", *Arth. and Rheumatism* 1989, 32:15–21.
Pregnancy, Autoimmunity and Connective Tissue Disorders, edited by Scott, J.S. and Bird, H.A., Oxford Univ. Press, Oxford, New York, Tokyo, 1990, p. 163–184.
Plauche, W.C., "Myasthenia Gravis", *Clin Obstet. Gynecol.* 1983, 26, 592–604.
Persellin, RH, "The Effect of Pregnancy on Rheumatoid Arthritis", *Bull. Rheum. Dis.* 1976, 77, 922–927.
Paulus et al., "Lymphocyte Involvement in Rheumatoid Arthritis", *Arthritis Rheum.* 1977, 20, 1249–1262.
Roullet et al., "Pregnancy and multiple sclerosis: A longitudinal study of 125 remittent patients", *J. Neurol. Neurosurg. Psychiatry* 1993, 56, 1062–1065.
Reiter et al., "Treatment of Rheumatoid Arthritis with Monoclonal CD4 Antibody M–T151", *Arthritis Rheum.* 1991, 34, 525–536.

(List continued on next page.)

*Primary Examiner*—Jean C. Witz
*Attorney, Agent, or Firm*—Seidel, Gonda, Lavorgna & Monaco, PC

[57] ABSTRACT

A method of treating autoimmune diseases is provided which involves administering an effective amount of allogeneic mononuclear cells or a molecule derived from these cells to an individual suffering from an autoimmune disease. Also provided are compositions for the treatment of autoimmune diseases.

5 Claims, No Drawings

OTHER PUBLICATIONS

Sadovnik et al., "Pregnancy and Multiple Sclerosis", *Arch. Neurol.* 1994, 51, 1120–1124.

Sany et al., "Immunomodulating Effect of Human Placenta–Eluted Gamma Globulins in Rheumatoid Arthritis", *Arthritis Rheum.* 1982, 25, 17–24.

Strand et al., "Effects of Administration of An Anti–CD5 Plus Immunoconjugate in Rheumatoid Arthritis", *Arthritis Rheum.* 1993, 36, 620–630.

Trentham et al., "Clinical and Immunologic Effects of Fractionated Total Lymphoid Irradiation in Refractory Rheumatoid Arthritis", *N. Engl. J. Med.* 1981, 305, 976–982.

Tumiati et al., "High–Dose Immunoglobin Therapy as an Immunomodulatory Treatment of Rheumatoid Arthritis", *Arthritis Rheum.* 1992, 35, 1126–1133.

Utz and McFarland, "The Role of T Cells in Multiple Sclerosis: Implications for Therapies Targeting the T Cell Receptor", *J. Neuropath Exp. Neurol.* 1994, 53, 351–358.

vanLaar et al., "Effects of Inoculation with Attenuated Autologous T Cells in Patients with Rheumatoid Arthritis", *J. Autoimmunity* 1993, 6, 159–167.

Varner, M.W., "Autoimmune Disorders and Pregnancy", *Semin. Perinatol.* 1991, 15, 238–250.

Wallace et al., "Plasmapheresis and Lymphoplasmapheresis in the Management of Rheumatoid Arthritis", *Arthritis Rheum.* 1979, 22, 703–710.

Van Walderveen et al., "Magnetic resonance evaluation of disease activity during pregnancy in multiple sclerosis", *Neurology* 1994, 44, 327–329.

Weyand et al., "The Influence of HLA–DRB1 Genes of Disease Severity in Rheumatoid Arthritis", *Ann. Int. Med.* 1992, 117:801–806.

Whitaker J.N., "Rationale for Immunotherapy in Multiple Sclerosis", *Ann. Neurol.* 1994, 36, S103–S107.

COMPOSITION AND METHOD FOR ALLOGENETIC MONONUCLEAR CELL IMMUNOTHERAPY

This is a division of application Ser. No. 08/476,698, filed Jun. 7, 1995, U.S. Pat. No. 5,674,487.

BACKGROUND OF THE INVENTION

Tens of millions of people in the United States suffer from rheumatoid arthritis (RA) or a related disease. While arthritis results in significantly fewer deaths as compared to cancer and cardiovascular diseases, there is no other group of diseases that causes so much suffering in so many people for such a prolonged period of time. Because of the tendency for arthritis sufferers to become disabled and even permanently crippled, this group of diseases is extremely important both socially and economically. There is presently no satisfactory cure for rheumatoid arthritis because its cause is unknown. In addition, many of the therapeutic agents administered to alleviate pain and inflammation associated with the disease, such as disease-modifying antirheumatic drugs (DMARDs) and non- steroidal anti-inflammatory agents (NSAIDs), produce intolerable side effects.

The understanding of the RA disease process has been considerably enhanced by the application of molecular immunology techniques. It is now generally accepted that rheumatoid arthritis represents a multifactorial disease with environmental factors (infectious agents or toxins), genetic susceptibility, and immune or autoimmune responses playing inter-connected roles. After initiation of the disease process, it is believed that activated T cells and their products are responsible for the progressive destruction of articular cartilage and sub-chondral bone that is characteristic of rheumatoid arthritis.

Advances in the understanding of the immunopathogenesis of rheumatoid arthritis have been coupled with immunologic strategies for treatment. Immunologic approaches to the treatment of rheumatoid arthritis are important and desirable given the potential toxicities associated with most remittive therapy in use today and the continued poor prognosis of rheumatoid arthritis despite aggressive drug treatment. Monoclonal anti CD4 antibodies have been used in the treatment of rheumatoid arthritis (Reiter et al., *Arthritis Rheum.* 1991, 34, 525–536; Horneff et al., *Arthritis Rheum.* 1991, 34, 129–140; Herzog et al., *J. Autoimmunity* 1989, 2, 627–642; Goldberg et al., *J. Autoimmunity* 1991, 4, 617–630). In these studies, involving approximately 30 patients, objective and subjective improvement was noted in nearly all cases.

Another study employed chimeric monoclonal antibody to CD4 to treat 25 patients with refractory rheumatoid arthritis (Moreland et al., *Arthritis Rheum.* 1993, 36, 307–318) and again, some beneficial effects were observed.

Immunotherapeutic approaches have also included leukapheresis, (Karsh et al., *Arthritis Rheum.* 1981, 24, 867–873; Wallace et al., *Arthritis Rheum.* 1979, 22, 703–710) thoracic duct drainage (Paulus et al., *Arthritis Rheum.* 1977, 20, 1249–1262) and total node irradiation (Trentham et al., *N. Engl. J. Med.* 1981, 305, 976–982). All of these modalities have resulted in varying degrees of improvement, but all also have obvious drawbacks.

Patients with rheumatoid arthritis have also been treated with one or more 5 day infusion courses with monoclonal anti-CD5 coupled to Ricin-A chain (Strand et al., *Arthritis Rheum.* 1993, 36, 620–630). In this open-label trial, improvement rates were 50–68% at one month and 22–25% at 6 months (two clinical trials were included). All patients produced antibodies against the anti-CD5 conjugate and most experienced a transient decrease in CD3/CD5 positive T cells with recovery after 2–4 weeks.

Since cytokines also play important pathophysiologic roles in rheumatoid arthritis, research into therapeutics has also focused in this area. Tumor necrosis factor (TNF$\alpha$) has received attention because it is consistently found in synovium of patients suffering from rheumatoid arthritis. In addition, anti-human TNF was demonstrated to prevent the development of arthritis in a transgenic human TNF$\alpha$ mouse model. Using chimeric (mouse-human) antibodies to TNF$\alpha$, twenty patients with active rheumatoid arthritis were treated (Elliott et al., *Arthritis Rheum.* 1993, 36, 1681–1690). Patients were given 20 mg/kg in divided doses weekly either over 2 or 4 weeks. They found overall improvement in the Ritchie Articular Index, joint count and C-reactive protein (CRP) levels, and reported no significant toxicity.

Immunization of patients having rheumatoid arthritis with autologous T cell lines established from cells obtained from RA synovial fluid (SF) and/or synovial tissue has also been shown to be of benefit in some patients (Kingsley and Verwilghen, *Clin. Exp. Rheumatol.* 1993, 11, S63–S64; Lohse et al., *J. Autoimmunity* 1993, 1, 121–130; vanLaar et al., *J. Autoimmunity* 1993, 6, 159–167).

Regarding treatment of humans with allogeneic mononuclear cells (MNC), patients receiving living-related renal transplants have been transfused with allogeneic blood in an attempt to limit the immune response. Similar therapies employing MNC have been applied in recurrent pregnancy loss since about 1981 based on the notion that the fetus represents an allogeneic "graft" and that women who have no demonstrable known cause for recurrent spontaneous abortion (RSA) are likely to be immunologically rejecting their fetuses. Since 1985, the inventor has immunized over 1500 women diagnosed as having RSA with MNC from their spouses. World-wide it is estimated that about 25,000 patients have received this treatment. No serious side effects from this treatment have been found.

Remission of rheumatoid arthritis occurs in about 70% of all pregnant women suffering from rheumatoid arthritis. Pregnancy induced remission was originally believed to be due to increased levels of cortisol but, clearly, it is not entirely due to hormonal effects. It has been observed that during pregnancy, women with rheumatoid arthritis who experience remission carry fetuses that are more disparate than similar to themselves with respect to class II alleles of the human leukocyte antigens HLA-DRB1, -DQA and -DQB (Nelson et al., *N. Eng. J. Med.* 1993, 329, 466–471). The immunologic mechanism(s) underlying this effect is not known; however, hypotheses include induction of suppressor mechanisms or displacement of arthritogenic peptides from maternal antigen presenting cells (APC) by fetal class II peptides thus subverting an arthritis-inducing immune response. Alternatively, maternal T cell recognition of specific allogeneic or fetal HLA-DR peptides may cause a switch from a predominantly proinflammatory response to one that is protective or suppressive.

While rheumatoid arthritis remains the prototype disease that improves during pregnancy, Multiple Sclerosis (MS) an autoimmune disease that affects about 160,000 women of child-bearing age in the U.S. (Davis and Maslow, *Obstet. Gynecol. Surv.* 1992, 47, 290–296) and that exhibits immunopathogenetic features similar to RA may be modulated by pregnancy. Pregnant patients with MS have been shown in retrospective studies to experience fewer exacerbations than non-pregnant historical controls and to have post-partum disease flares (Davis and Maslow, *Obstet. Gynecol. Surv.* 1992, 47, 290–296; Abramsky, O., *Ann. Neurol.* 1994, 36, S38–S41; Hutchinson, M., *J. Neurol. Neurosurg. Psychiatry,* 1993, 56, 1043–1045). Prospective studies of MS patients have confirmed the retrospective analyses (Bernardi et al., *Acta Neurol. Scand.* 1991, 84, 403–406; Birk et al., *Arch. Neurol.* 1990, 47, 738–742; Roullet et al., *J. Neurol. Neurosurg. Psychiatry* 1993, 56, 1062–1065; Sadovnik et al., *Arch. Neurol.* 1994, 51, 1120–1124). Furthermore, brain lesions in MS demonstrated by magnetic resonance have been shown to improve during pregnancy and return to the pre-pregnancy state in the postpartum period (van Walderveen et al., *Neurology* 1994, 44, 327–329) Like RA, MS has been treated with immunosuppressive drugs and more recent trials have included the use of monoclonal antibodies to T cell subsets, T cell receptors, cytokines, and adhesion molecules (Whitaker J. N., *Ann. Neurol.* 1994, 36, S103–S107; Utz and McFarland, *J. Neuropath. Exp. Neurol.* 1994, 53, 351–358). Recent studies demonstrate that a synthetic CD4 peptide analog inhibits experimental allergic encephalomyelitis (EAE) in a mouse model (Jameson et al., *Nature* 1994, 368, 744–746). Immunomodulation using both alpha- and beta-interferon have undergone clinical trials (Durelli et al., Neurology 1994, 44, 406–413; Connelly, J. F., *Ann. Pharmacother.* 1994, 28, 610–616).

Spondyloarthropathies (HLA-B27 related diseases) are more common in males than in females. However, ankylosing spondylitis (AS), psoriatic arthritis (PS), and Reiter syndrome (RS) can affect women in the child-bearing age. Approximately 20% of patients suffering from the connective tissue disorder ankylosing spondylitis also experience remission of symptoms during pregnancy (Ostensen and Husby, "Seronegative spondylarthritis and ankylosing spondylitis: Biological effects and management", Pregnancy, Autoimmunity and Connective Tissue Disorders, edited by Scott, J. S. and Bird, H. A., Oxford Univ. Press, Oxford, N.Y., Tokyo, 1990, p. 163–184). In addition, while a systematic study of pregnancy effects on Psoriatic arthritis (PA) has not been reported, it is of interest that one of the pregnancy induced remission patients initially described by Hench in *Mayo Clin. Proc.* 1938, 13, 161–167 had PA.

In addition, the organ-specific autoimmune disease, Myasthenia gravis (MG), has been shown to have a variable response during pregnancy with about 30% of patients experiencing remission and 40% experiencing exacerbation (Varner, M. W., *Semin. Perinatol.* 1991, 15, 238–250; Plauche, W. C., *Clin. Obstet. Gynecol.* 1983, 26, 592–604).

The known phenomenon of pregnancy-induced remission and post partum exacerbation of rheumatoid arthritis (Persellin, RH, *Bull. Rheum. Dis.* 1976, 77, 922–927) led to the use of gamma globulin eluted from placentas in the treatment of rheumatoid arthritis. In one study, 11 patients were treated with placenta-eluted gamma globulin and improvement was noted in seven of these patients (Sany et al., *Arthritis Rheum.* 1982, 25, 17–24). High dose intravenous immunoglobulin (IVGG) has also been shown to be effective in modulating the course of rheumatoid arthritis (Tumiati et al., *Arthritis Rheum.* 1992, 35, 1126–1133). Ten patients with active, severe rheumatoid arthritis were treated with 6 monthly infusions. All patients showed improvement; however, all patients also relapsed within weeks of the last infusion.

It has now been found that treatment of patients with active rheumatoid arthritis by immunization with allogeneic MNC can result in amelioration of symptoms and improvement in disease activity indices. This treatment approach was taken in order to determine if the beneficial effects of pregnancy on these autoimmune diseases could be duplicated in non-pregnant patients. Treatment with allogeneic MNC can also be used in the treatment of a number of autoimmune disease, including, but not limited to, Multiple Sclerosis, Spondyloarthropathies, and Myasthenia Gravis.

SUMMARY OF THE INVENTION

An object of the present invention is to provide a method of treating autoimmune diseases which comprises administering an effective amount of allogeneic mononuclear cells or molecules derived from these cells to an individual suffering from an autoimmune disease.

Another object of the present invention is to provide a composition for the treatment of autoimmune diseases comprising purified allogeneic white blood cells or molecules derived from these cells.

DETAILED DESCRIPTION OF THE INVENTION

Administration of an effective amount of allogeneic white blood cells or molecules derived from these cells can be used to treat patients suffering from a number of different autoimmune diseases. Examples of autoimmune diseases which can be treated by administration of these cells include, but are not limited to, rheumatoid arthritis, Multiple Sclerosis, Spondyloarthropathies, and Myasthenia Gravis. This treatment can also be used as an adjunct to immunosuppressive drug treatment of organ graft recipients.

By "effective amount" it is meant a concentration of allogeneic mononuclear cells or molecules derived from these cells which, when administered to a patient suffering from an autoimmune disease, produce a beneficial effect. For example, in patients suffering from rheumatoid arthritis, approximately 80 to 100 million cells administered in a standard buffered salt solution (Lactated Ringers solution) at 6–8 week intervals has been found to be an effective amount, alleviating patient suffering.

Allogeneic MNC has been administered to 10 female patients with active rheumatoid arthritis. In each instance, MNC were obtained from the patient's spouse or an individual chosen by the patient. In this first trial, patients received a series of at least 3 injections of approximately $10^8$ MNC at 6 week intervals. No adverse effects were noted in any of the patients. Clear improvement in at least 2 of the parameters measured occurred in 7 of 10 patients. Table 1 shows results of Arthritis Impact Measurement Scales (AIMS) scores, which provides a numerical means of following disease activity, physician global assessments, patient assessment of pain, swollen joint counts, and erythrocyte sedimentation rate (ESR) and/or C-reactive protein (CRP) determination in a number of patients entered.

TABLE 1

Measure of Disease Activity in Patients in the Preliminary Trial of Allogeneic Mononuclear Cell Immunization for Rheumatoid Arthritis

| Patient | MNC Treatment | No. Cells given ($\times 10^{-6}$) | ESR or CRP | Physician Global Assess. | Patient Assess. of Pain | AIMS score | Swollen Joint Count |
|---|---|---|---|---|---|---|---|
| S. M. | Immuniz. #1 | 227 | 50 mm/hr | 59 | 67 | 37.36 | 11 |
|  | Immuniz. #2 | 180 | 39 | 40 | 68 | 44.15 | 8 |
|  | Immuniz. #3 | 95 | 28 | 18 | 22 | 20.58 | 4 |
| R. E. | Immuniz. #1 | 78 | 2.49 mg/dl | 88 | 81 | 55.35 | 12 |
|  | Immuniz. #2 | NR** | 5.43 | 53 | 90 | 59.12 | 10 |
|  | Immuniz. #3 | NR | 2.53 | 47 | 45 | 45.87 | 8 |
| J. B. | Immuniz. #1 | 97 | 50 mm/hr | 43 | 25 | 53.06 | 8 |
|  | Immuniz. #2 | 55 | 66 | 27 | 16 | 37.38 | 11 |
|  | Immuniz. #3 | 150 | 47 | 16 | 30 | 36.09 | 4 |
| L. C. | Immuniz. #1 | 175 | 34 mm/hr | 51 | 42 | 41.60 | 12 |
|  | Immuniz. #2 | 165 | NA | 21 | 10 | 34.90 | 12 |
|  | Immuniz. #3 | 80 | 21 | 23 | 17 | 27.94 | 6 |
| R. H. | Immuniz. #1 | 180 | 10 mm/hr | 35 | 36 | 30.52 | 14 |
|  | Immuniz. #2 | 105 | 15 | 20 | 2 | 21.57 | 4 |
|  | Immuniz. #3 | 150 | 31 | 25 | 52 | 32.86 | 12 |
| W. V. | Immuniz. #1 | 75 | 8 mm/hr | 58 | 78 | 65.71 | 8 |
|  | Immuniz. #2 | 44 | 9 | 62 | 85 | NA | 7 |
|  | Immuniz. #3 | 120 | 6 | 34 | 78 | 73.21 | 8 |
| B. C. | Immuniz. #1 | 113 | 43 mm/hr | 45 | 72 | ND | 4 |
|  | Immuniz. #2 | 98 | 42 | 45 | 74 | 33.17 | 3 |
|  | Immuniz. #3 | 62 | 61 | 30 | 90 | 49.87 | 3 |
| L. M. | Immuniz. #1 | 146 | 4.75 mg/dl | 37 | 45 | 35.45 | 6 |
|  | Immuniz. #2 | 66 | 3.84 | 35 | 51 | 41.85 | 5 |
|  | Immuniz. #3 | 68 | N.D. | 45 | 59 | 43.37 | 3 |
| M. O. | Immuniz. #1 | 75 | 26 mm/hr | 75 | 81 | 50.90 | 18 |
|  | Immuniz. #2 | 37 | 20 | 52 | 65 | 43.80 | 6 |
|  | Immuniz. #3 | 99 | 22 | 60 | 61 | 48.44 | 16 |
| M. R. | Immuniz. #1 | 84 | 65 mm/hr | 35 | 63 | 34.61 | 15 |
|  | Immuniz. #2 | 93 | 84 | 41 | 64 | 41.82 | 5 |
|  | Immuniz. #3 | 140 | 48 | 37 | 51 | 32.17 | 3 |

In Table 1, ESR (erythrocyte sedimentation rate) is measured in mm/hr. CRP (C-reactive protein) is measured in mg/dl. ND means "not measured".

A summary of clinical disease activity assessments on the ten patients who have completed a series of three MNC treatments at 6 week intervals is provided in Table 2. Each separate analysis revealed statistically significant improvement at 95% confidence (paired Student's test).

TABLE 2

Mean Values of Disease Activity Measurements
in Ten Patients Before and After Completing
Three MNC Immunizations for Rheumatoid Arthritis

|  | AIMS Score | Physician Global Assess. | Patient Assess. of Pain | Swollen Joint Count |
|---|---|---|---|---|
| Before | 44.98 | 52.6 | 59.0 | 10.8 |
| After | 40.06 | 33.5 | 52.3 | 6.6 |
| p Value | <.02 | <.001 | <.006 | <.001 |

It may be that class II major histocompatibility (MHC) gene products are responsible for the beneficial effect in RA observed after MNC treatment, just as it is class II disparity between a mother an fetus that appears to induce pregnancy-associated remission of RA. The genes of the major histocompatibility complex direct the synthesis of proteins that can be found on the surfaces of most cells. These proteins are referred to as the human leukocyte antigens (HLA) or sometimes as "MHC determinants". HLA are molecules that determine individuality within a species, bind and present antigens to immunocompetent cells, and are targets of graft rejection by immune effector cells. Thus, HLA are both necessary for immune responses to occur in individuals and can be targets of immune responses. HLA can bind an individual's own proteins and present these to the immune system. In some individuals this may result in autoimmune disease. MHC genes also determine susceptibility to certain diseases, for example, rheumatoid arthritis. HLA are designated class I or class II, based on their structure. Class I HLA are comprised of a single transmembrane alpha chain associated with beta-2 macroglobulin ($\beta$-2m) and usually interact with CD8+ cytotoxic T cells. Class II HLA have both alpha and beta transmembrane heavy chains and interact with CD4+ T cells that mediate helper and inducer effects and delayed-type hypersensitivity which is the classical histopathology of RA. Class I HLA antigens are present on virtually all nucleated cells in the body and are highly expressed on cells of the immune system. Class II HLA antigens are restricted in their distribution and are found predominantly on certain cells of the immune system. Relevant to the present invention, T cells express only class I antigens while B lymphocytes and monocytes express both class I and II antigens. These types of cells can be isolated from each other by depleting one or the other groups of cells thereby providing two sets of cells for comparison in immunization procedures. MNC prepared form whole blood contain T cells, B cells and monocytes. Only T cells remain when MNC is treated with an antibody directed against class II HLA antigens. An example of such an antibody is the monoclonal antibody known as L243. Only B cells and monocytes remain if MNC is treated with a monoclonal antibody that only reacts with T cells. Anti CD3 is one example of such an antibody.

Patients suffering from an autoimmune disease such as rheumatoid arthritis, Multiple Sclerosis, Spondyloarthropathies, Myasthenia Gravis may be treated with whole MNC populations (containing monocytes, B cells and T cells) or a sub-population of MNC. Either the population of B cells plus monocytes (positive for both class I and class II HLA molecules or the population of T cells (positive for class I but not class II HLA) are believed to mediate the effects. There are several means by which these cells can be effectively separated from each other which are routine to those of skill in the art including, but not limited to, magnetic cell sorting that employs a device and reagents manufactured by Immunicon Corp. (Reg) Huntington Valley, PA. In one embodiment, MNC are treated with formalin to increase antigenicity of the cells and negate the possibility of these cells causing graft vs. host disease in an immunocompromised individual.

It is also believed that a beneficial effect can result from the treatment of patients suffering from an autoimmune disease with purified class I or class II molecules. Presentation of these molecules on the allogeneic cell surface is not required. Thus, compositions comprising purified class I and/or class II HLA molecules from single, selected or pooled donor white blood cells; portions of class I and/or II molecules (attenuated molecules or peptides) fractionated from whole molecule preparations; and synthetically prepared peptides or larger molecules based on the knowledge of amino acid sequence and structure studies of the class I or II molecules may be administered.

In a preferred embodiment, compositions of the present invention which contain molecules as described above are presented to the patient with the patients own mononuclear cells. For example, cells of specifically identified donors or the patient's own cells which are obtained, treated with the composition and reinjected into the patient, can be used. The composition can be attached to the patient's own mononuclear cells in a number of ways, including chemical attachment of the relevant product to the patient's cells, and attachment of the relevant product to the cells. In a preferred embodiment monocytes are used, as these cells have the capability of binding the class I or class II molecules/peptides as one of their normal functions. The procedures required to produce compositions of the present invention are routine to an individual skilled in the arts of immunology and molecular biology/chemistry.

Methods of identifying appropriate patient donor pairs which increase the probability of the alloimmunization treatment being effective in a selected patient have also been developed. These methods are based upon the measurement of specific differences between histocompatibility genes or antigens expressed on the MNC of donors and patients or in vitro immune responses of patient T lymphocytes to donor MNC or MNC membrane extracts or by determining the presence of antibodies directed against MNC membrane extracts either before immunization or following the first treatment.

Susceptibility to the development of RA has been suggested to be related to a sequence of DNA that is found as an allelic variant in the third hypervariable region of HLA DR4 beta chain (DRB1) (Nepom et al., *Arth. and Rheumatism* 1989, 32:15–21; Weyand et al., *Ann. Int. Med.* 1992, 117:801–806). These sequences, known as DRB1*0401*0404 and *0408, have been identified using sequence specific oligonucleotide probes (SSOP) in DNA extracts of leukocytes from RA patients. The allelic variants are believed to either encode an HLA class II peptide that binds an arthritogenic substance or to encode a self class II peptide that stimulate arthritogenic T cell clones. Since the beneficial effect of alloimmunization of RA patients and patients suffering from an autoimmune disease may be based upon specific differences between DRB DNA of donors and patients, DNA based tissue typing using SSOP can provide an indicator as to who will and who will not respond to treatment. For example, if donor and patient shared or had closely related DRB1*0401 sequences than a beneficial effect of immunization would not be expected, whereas if they were significantly different, alloimmunization would be expected to be more effective.

Patients can also be selected for immunotherapy or donor-patient pairs on the basis of a patient's lymphocyte responses to a panel of donor lymphocytes or to donor MNC membrane extracts. Patient MNC can be cultured with donor MNC or membrane extracts and the cell proliferation can be measured by conventional methods such as [$^3$H]-thymidine incorporation or IL-2 production by responding cells. In addition, culture supernatants from the donor-patient MNC pairs can be tested for the presence of TH2-related cytokines such as IL-4, IL-10 and TGFβ. These cytokines are primarily suppressive of delayed-type hypersensitivity reactions which represents the immunopathology round in RA joint tissues. Thus, appropriate donor patient-pairs can be selected by determining which donor stimulates the strongest production of TH2 cytokines by patient lymphocytes.

Patient sera can also be tested for the presence of antibody to pooled MNC extracts. Using an enzyme linked immunosorbent assay (ELISA) and Western blotting, IgG and IgM antibodies against MNC membrane extracts were detected. Pooled MNC from 10 or more donors were used for the preparation of membrane extracts in accordance with the procedure described by Goldberg et al., *Am. J. Reprod. Immunol.* 1995 33:21–30. The membrane extracts was then used as the target antigen in an ELISA and as the antigen source in a polyacrylamide gel electrophoresis (PAGE) followed by Western blotting using patient sera as a source of antibody. Results of binding in ELISA and of finding antibodies in sera, when correlated to beneficial alloimmunization outcomes can provide another means of patient selection.

The following examples are provided for illustrative purposes only and are not intended to limit the invention in any way.

EXAMPLES

Example 1: Patient Profiles and Disease Assessment

Ten patients were treated in the first trial. None of the patients were receiving concomitant treatment with disease modifying anti-rheumatic drugs (DMARDs), and only one was receiving a small dose of prednisone (<10 mg/day). If patients were taking DMARDs, this treatment was discontinued for 6 weeks prior to entry into the immunotherapy trial. Disease activity was assessed clinically by patient global assessment of pain, physician global assessment of disease activity, AIMS questionnaire and swollen joint counts. Laboratory assessment included hematologic profile with platelet counts, erythrocyte sedimentation rate (ESR) and/or C-reactive protein determination (CRP). These parameters were recorded prior to entry into the study and 6 weeks thereafter including 6 weeks after the last injection of MNC in 2 patients and 9 months after the last injection in one patient. The latter patient has had no recurrence of active rheumatoid arthritis, the other two patients had evidence of active rheumatoid arthritis 6 weeks after the last injections. One of those patients, JB, improved after immunotherapy was reinstituted.

Example 2: Isolation of MNC

In each instance MNC were obtained from the patient's spouse or an individual chosen by the patient. MNC donors were screened for liver enzyme abnormalities, hepatitis B and C, human immunodeficiency viruses 1 (HIV-1) and 2 (HIV-2) and human T lymphotropic virus 2 (HTLV-2). Blood (100–120 ml) was obtained from the donors by venipuncture. This amount of blood usually yields between 80 and 150×10$^6$ MNC after ficol-hypaque centrifugation. After washing in Earle's balanced salt solution, MNC were resuspended in 4 ml lactated Ringer's solution. Two ml were injected intravenously (IV) and the remaining 2 ml in divided doses of 0.5 ml each subcutaneously (SQ), at 4–6 week intervals. Clear improvement in at least 2 of the parameters measured occurred in 7 of 10 patients.

Example 3: Treatment Protocol in Larger Clinical Trials

Patients are divided into two groups, each group receiving a series of six treatments by intravenous bolus injection or subcutaneous injection. The patients in each group will be randomly assigned to receive different types of MNC. The randomization assignment is accomplished by a computer program so that by chance alone a patient will receive either MNC that are all positive for only class I HLA antigens (T cells) or MNC that are all positive for both class I and class II HLA antigens (B cells and monocytes). Immunizations will be performed at 6 week intervals using 80–100×10$^6$ cells each time. Patients in whom a beneficial effect is seen after 6 injections, are treated on a continuing basis but with graduated (2 weeks) lengthening of the interval between injections in order to determine the maximum time period that can elapse between treatments.

In the alternative, patients can also be randomized to receive allogeneic cells or a placebo such as autologous cells, i.e., their own cells, or saline injections in a randomized, double-blind placebo controlled prospective trial.

Example 4: Criteria for Assessing Clinical Outcome

Clinical outcomes are assessed using the American College of Rheumatology (ACR) core criteria for disease activity. Six of these criteria are applied prior to study entry and at 6 week intervals during and for up to 12 weeks after completion of the trial. The criteria include swollen joint count, AIMS score, physician global assessment of disease activity (10 cm analog scale), patient assessment of pain (10 cm analog scale) and acute phase reactant value (ESR and/or CRP).

Example 5: Collection of MNC

When donor screening tests are complete, donors are scheduled with the TJU Blood Donor Center for obtaining a "buffy coat". MNC (300–500×10$^6$) are recovered from "buffy coats" by ficol hypaque centrifugation. For patients randomized to receive only class I positive cells, class II positive cells are depleted using supernatants of the L243 anti HLA-DR hybridoma cell line which is well known in the art. Patients randomized to receive class I and II positive cells receive cells magnetically depleted of CD3+ MNC. Cells prepared for immunization are labeled and stored in liquid nitrogen in 90% fetal calf serum (FCS)/10 dimethyl sulfoxide (DMSO) until used for patient treatment. Greater than 90% of cells frozen in this manner are recovered.

What is claimed:

1. A pharmaceutical composition for treatment of an autoimmune disease comprising a pharmaceutically acceptable carrier and an effective amount of purified formalin-treated mononuclear cells obtained from a healthy human donor.

2. The composition of claim 1 wherein the autoimmune disease comprises rheumatoid arthritis, Multiple Sclerosis Spondyloarthropathies, or Myasthenia Gravis.

3. The composition of claim 1 wherein the cells are B cells.

4. The composition of claim 1 wherein the cells are monocytes.

5. The composition of claim 1 wherein the cells are T cells.

* * * * *